United States Patent
Frezza

[11] Patent Number: 5,807,346
[45] Date of Patent: Sep. 15, 1998

[54] METERING INSTRUMENT, PARTICULARLY FOR INJECTING MEDICINAL LIQUID

[75] Inventor: Pierre Frezza, Charly, France

[73] Assignee: Laboratoire Aguettant, Lyon, France

[21] Appl. No.: 500,951

[22] PCT Filed: Feb. 7, 1994

[86] PCT No.: PCT/FR94/00137

§ 371 Date: Sep. 8, 1995

§ 102(e) Date: Sep. 8, 1995

[87] PCT Pub. No.: WO94/17846

PCT Pub. Date: Aug. 18, 1994

[30] Foreign Application Priority Data

Feb. 8, 1993 [FR] France .................................. 93 01557

[51] Int. Cl.⁶ .................................................. A61M 5/00
[52] U.S. Cl. .......................... 604/208; 604/209; 604/232
[58] Field of Search ........................... 604/206–211, 218, 604/224, 228, 232, 241

[56] References Cited

U.S. PATENT DOCUMENTS

| | | | |
|---|---|---|---|
| 4,865,591 | 9/1989 | Sams | 604/186 |
| 4,973,318 | 11/1990 | Holm et al. | 604/208 |
| 5,084,017 | 1/1992 | Maffetone | 604/110 |
| 5,158,549 | 10/1992 | McCarthy | 604/110 |
| 5,279,585 | 1/1994 | Balkwill | 607/207 |

FOREIGN PATENT DOCUMENTS

| | | |
|---|---|---|
| 037 696 | 10/1981 | European Pat. Off. . |
| 416 975 | 3/1991 | European Pat. Off. . |
| 496 141 | 7/1992 | European Pat. Off. . |
| 498 737 | 8/1992 | European Pat. Off. . |
| 1170312 | 1/1959 | France . |
| 91 10460 | 7/1991 | WIPO . |

Primary Examiner—Wynn Wood Coggins
Assistant Examiner—A. T. Nguyen
Attorney, Agent, or Firm—Oliff & Berridge, PLC

[57] ABSTRACT

A metering instrument for dispensing several doses of a liquid includes a tubular body designed to be held by the user, a reservoir containing the liquid, a movable tail mounted inside and on the axis of body, and a pusher grippable by the user and mounted translationally in the body. The tail has a rack constituted by successive annular notches, and the body has several axial slots distributed over its periphery. The pusher includes an outwardly projecting pin that is designed to engage one of the axial slots of the body.

22 Claims, 2 Drawing Sheets

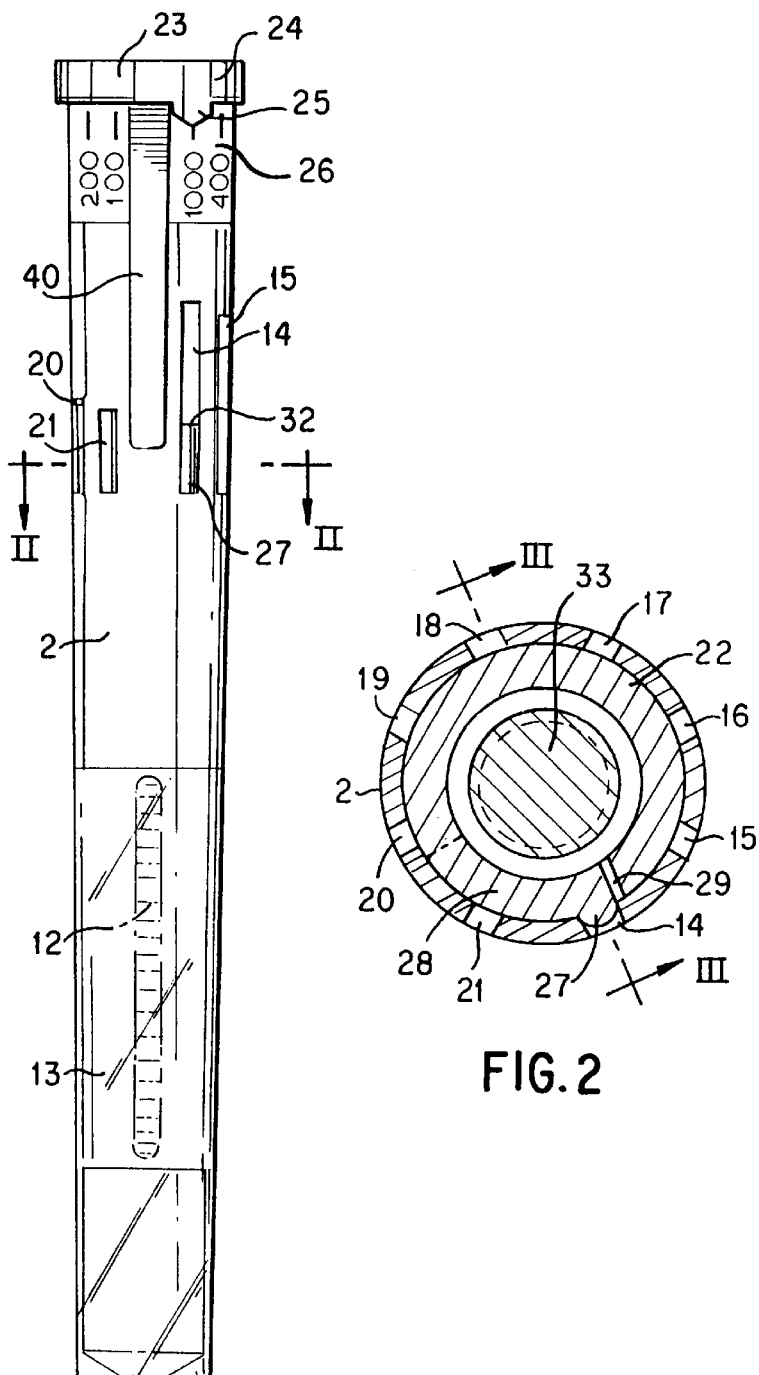
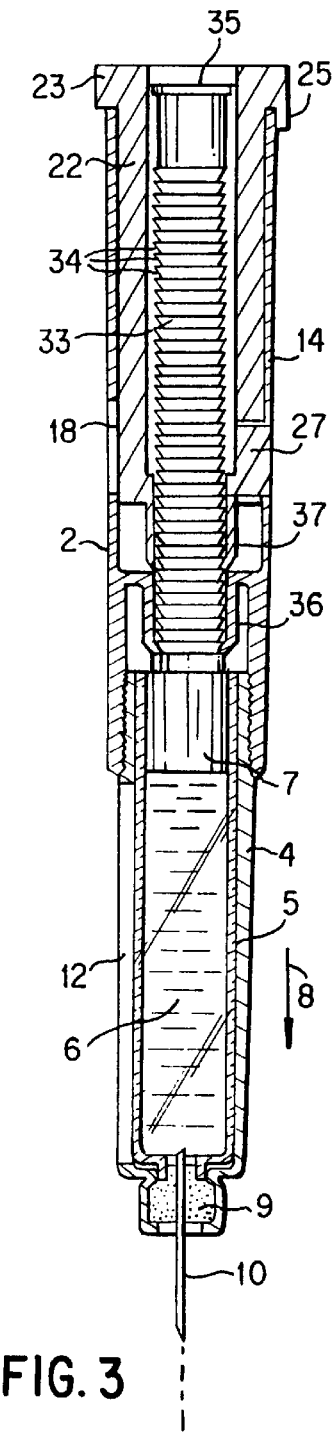

METERING INSTRUMENT, PARTICULARLY FOR INJECTING MEDICINAL LIQUID

BACKGROUND OF THE INVENTION

The present invention relates to a metering instrument, particularly for medicinal liquid, allowing successive dispensing of several doses of a liquid or other fluid, from a load or refill.

This instrument relates nonexclusively to an injection instrument of the syringe type allowing parenteral administration or self-administration of several doses of a medicinal liquid drawn from an ampule such as an ampule of the "Carpule" type, which is a glass, rubber-stoppered cartridge containing local anesthetic solutions, fitted in a special syringe for hypodermic injection.

Description of the Prior Art

Document FR-A-1,170,312 relates to a syringe-type injection device in which the rod of the plunger is actuated by a rack, said rack being driven in the injection direction by a first ratchet device, and is held back in the opposite direction of motion by a second ratchet device.

Document EP-A-0,416,975 relates to a device allowing several injections to be given from the same refill, comprising a tubular body designed to be held by the user, a reservoir containing the liquid load, disposed at one end of the body, a pusher mounted coaxially and free to move translationally inside the body, activatable by the user by one of its ends, which projects beyond the body on the side opposite the reservoir, a tail in the shape of a helical rack, mounted inside the pusher, having one end resting on the bottom of the reservoir. A first ratchet means, associated with the body, allows the tail to move in the injection direction but not in the reverse direction, while a second ratchet means associated with the pusher engages the tail when the latter moves in the injection direction, and releases the tail when the pusher is moved in the other direction.

The volume of the injected dose is determined essentially by the number of clicks corresponding to passage of the notches of the tail along the ratchet means associated with the body. This solution is totally unsatisfactory, in that it offers no safety, particularly when the person who must self-administer an injection is a handicapped person or has lost manipulation skills or who, in an emergency, must very quickly inject a predetermined dose of an active principle.

Another solution consists of having a mechanism for adjusting the initial position of the pusher establishing the translational travel of the latter relative to the tail, this translational adjustment being effected by means of a helical external thread incorporated into the tail, engaged by an interior notch provided on the pusher, whereby rotation of the pusher relative to the tail allows said pusher to be retracted inside the body or extended therefrom for an adjustable distance. This change in the axial starting position of the pusher determines the travel thereof relative to the body and hence the volume of the injection dose.

The latter device has a large number of parts that cannot be joined together automatically, resulting in a high cost price incompatible with single use. Under these conditions, such an instrument cannot be disposable.

Moreover, the way in which it is used remains complicated and, like the device described previously, it cannot be used by handicapped persons who do not have all their faculties, or in an emergency when a dose must be injected very rapidly.

SUMMARY OF THE INVENTION

The goal of the invention is to furnish a metering instrument for injecting medicinal liquid, of simple design, made with a small number of parts, assemblable very rapidly and automatically, ergonomic, offering high precision in the volume of the dispensed or injected dose, and with the possibility of setting to several different dose volumes.

For this purpose, the instrument to which it relates, of the type comprising:

a tubular body designed to be held by the user, a reservoir containing the liquid load or refill, built onto or into said body, said reservoir having a tubular wall on the axis of the body, a plunger forming a seal, closing off one end of said tubular wall, displaceable toward the other end in a direction known as a reference direction, and a perforable stopper closing off the other end through which a dose of the liquid passes, a tubular pusher mounted coaxially and free to move translationally inside the body, activatable by the user by one of its ends which projects beyond the body, a tail forming a rack, mounted inside and on the axis of the pusher, having one end abutting the plunger of the reservoir, a first ratchet means disposed on the body, disengaged from the tail in the reference direction and engaging the tail in the other direction, and a second ratchet means disposed on the pusher, engaging the tail in the reference direction, and disengaged from said tail in the other direction, is characterized in that the cylindrical tail has a plurality of successive annular notches provided on the axis of the body, over a length at least equal to the plunger travel necessary for emptying the reservoir, cooperating both with the first ratchet means and the second ratchet means, in that the body has several axial slots of different lengths, distributed over the periphery of the body, and in that the pusher has a pin which projects from its outer surface and is designed to engage one of the slots in the body, the length of which corresponds to the travel chosen for the pusher.

The ratchet means of the body and those of the pusher on the rack of the tail are constituted by series of teeth molded onto the body and the pusher respectively, each tooth being designed to penetrate between two successive notches of the rack. The number of component parts of this instrument is hence small, since it comprises essentially the body, the pusher, and the tail. The body is in one piece and provides the function of metering, because of its various slots, pawl function, and display of the dose indicated opposite each slot.

The pusher has the functions of loading, injection, reading of the dose setting, and adjusting the dose, as well as pawls because of its ability to apply pressure to the tail when the plunger is depressed and to slide along the tail when a movement in the reverse direction takes place.

The tail forming a rack has the functions of driving the plunger, preventing its return, and metering, the minimum injection unit being equal to the length of one notch.

Since the body and the pusher are tubular and open at their ends, they are assembled simply by fitting them together and positioning of the tail is effected simply by engagement inside the pusher, from the outside, toward the pusher end located on the reservoir side. Assembly is extremely simple and may be automated.

It is important to note that, because of the circular cross section of each notch of the rack, it is possible to pivot the pusher around the tail, inside the body, to move the pin integral with the pusher from one of the slots of the body to another, to change the dose volume.

Advantageously, the length of each axial slot provided in the body affords pin travel equal to a whole number multiplied by the length of a notch on the rack provided on the tail.

According to another characteristic of the invention, the pin projecting from the outer surface of the pusher is designed to retract radially when the pusher is driven rotationally in one direction inside the body, and/or axially when the pusher is introduced inside the body.

For this purpose, the pin that projects from the outer surface of the pusher is comprised of an axial rib that projects outward, provided at the free end of a tongue delimited in the wall of the pusher by an axial slot and two circumferential slots extending over part of the periphery of the pusher.

When the pusher is driven rotationally inside the body, in one rotational direction, the tongue carrying the pin tends to tilt inward, allowing the pin to retract along the inside wall of the body.

In addition, to facilitate introduction of the pusher inside the body, the edge of the rib forming a pin, located forward in the direction of introduction of the pusher into the body, is rounded, while the rear edge of this rib is straight and perpendicular to the pusher axis.

According to another characteristic of the invention, the end of the pusher outside the body and activatable by the user is equipped with a collar designed to abut the rear edge of the body, at the end of the injection travel.

This collar allows the pusher to be pulled and pushed, to load and inject respectively, and be turned to set the injector to the dose volume to be dispensed.

Advantageously, the various slots provided in the body have front ends located in a plane perpendicular to the axis of the body, the distance between this plane and the rear end of the body being slightly greater than the distance between the front edge of the pin provided on the pusher and the collar disposed at the rear end of the pusher.

As a result of this characteristic, at the end of the forward travel of the pusher, the collar of the latter abuts the upper edge of the body before the pin contacts the lower end of the slot in which it is displaceably mounted. This guarantees a distinct end of travel and hence precision of the injected volume.

To facilitate reading the dose volume, the collar of the pusher is equipped with a pointer aligned with the pin and oriented in the forward direction, which pointer is opposite a marking on the body aligned with each slot. At its upper end, the tail is equipped with a collar whose outside diameter is less than the inside diameter of the pusher, but does not allow passage of the ratchet means of the pusher.

Thus, the operator is immediately alerted when the volume of liquid available and remaining in the reservoir is less than the volume of the dose to be injected. Also, it is not possible, after removal of the reservoir, to withdraw the tail comprising the rack at the front, so that the instrument is not reusable.

BRIEF DESCRIPTION OF THE DRAWINGS

One embodiment of this instrument is described hereinbelow with reference to the schematic drawing attached wherein:

FIG. 1 is a front view of this injection instrument of the fountain pen-injector type before the first use, when the reservoir is full;

FIG. 2 is a cross-sectional view on an enlarged scale according to line II—II in FIG. 1;

FIG. 3 is a lengthwise section along line III—III in FIG. 2, after removal of the cap;

DESCRIPTION OF PREFERRED EMBODIMENTS

Figure 4:
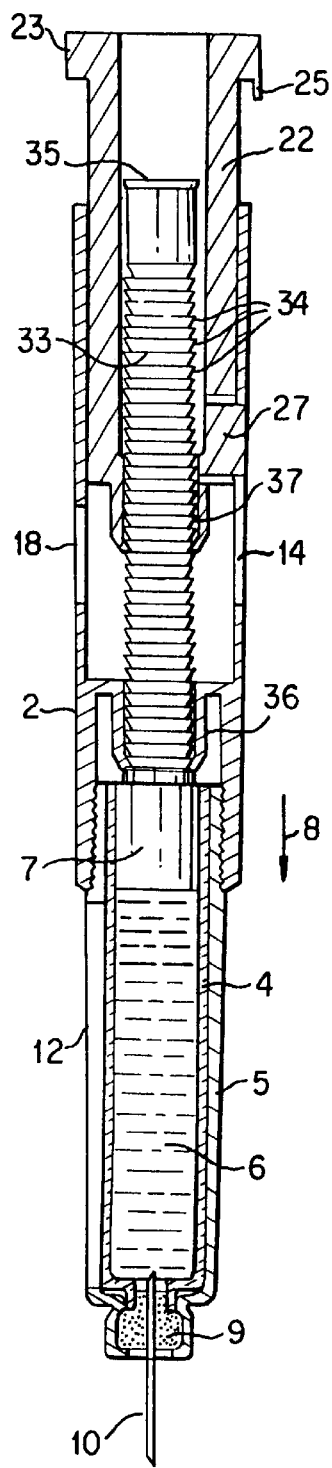
FIGS. 4 and 5 are two lengthwise sections similar to FIG. 3, during two phases of use.

The instrument shown in the drawing comprises a tubular body 2 with a circular cross section, made of synthetic material, having in the vicinity of its forward end an internal thread 3 to receive, by screwing, an envelope 4 containing a reservoir 5 or Carpule for the medicinal liquid 6 to be injected. Carpule 5 is closed at its rear end by a plunger 7. This plunger is displaceable in one direction called reference direction 8 corresponding to the emptying direction of the Carpule. Another plug 9 closes off the other end of the Carpule which is traversed by an injection needle 10. Envelope 4 has a lengthwise slot 12 for inspecting the liquid level inside the Carpule.

As shown in FIG. 1, a removable cap 13 covers the forward end of the instrument, the chief function of which is to protect needle 10 against two successive uses of the instrument.

As shown in particular in FIGS. 1 and 2, the body has a number of lengthwise slots, eight in the example shown, numbered 14–21.

The instrument also has a tubular pusher 22 with a circular cross section, open at both its ends, constituted by a molded part of synthetic material, designed to slide and pivot inside body 2.

This pusher 22 has, at its upper end, namely at its end opposite the end facing reservoir 5, a collar 23 for loading and injection of a dose. This collar 23 has, for reasons of ease in manipulation, an external knurling 24, and has a pointer 25, directed toward the front of the instrument, able to assume a position in which it overrides the exterior of the body at the end of the injection, and cooperating with markings 26 provided on the body to show the volume of the dose injected or to be injected.

Opposite pointer 25, pusher 22 has a pin 27 which projects outward, designed to engage a slot 14–21 in the body. Pin 27 is constituted by an axial rib projecting outward, provided at the free end of a tongue 28, delimited in the wall of the pusher by an axial slot 29, and by two circumferential slots 30. Moreover, the front edge of pin 27 is rounded, while its rear edge 32 is perpendicular to the axis of the pusher.

This instrument also has a tail 33 made of synthetic material, with a cylindrical cross section, having over its height a plurality of successive annular notches forming a rack whose length is at least equal to the travel of plunger 7 of carpule 5. The cross section of each notch 34 decreases from the rear to the front, namely in reference direction 8. Tail 33 has a smaller cross section than the inside cross section of pusher 22 and is designed to engage the latter from back to front. The upper end of tail 33 is equipped with a collar 35.

Body 2 on the one hand and pusher 22 on the other hand each have, in the vicinity of their lower ends, a series of teeth, 36 and 37 respectively. Teeth 36 of one series are located in a plane perpendicular to the axis of the instrument, and teeth 37 of the other series are also disposed in the same plane. Each tooth 36, 37 is oriented radially inward and inclined in the direction of the end of the body containing reservoir 5. Each tooth is designed for penetration between two successive notches 34 of the rack.

As a result of the structure of body 2, pusher 22, and tail 33, when pressure is exerted on pusher 22 in reference direction 8 it drives the tail, which passes freely between teeth 36 of body 2. On the contrary, when the pusher is withdrawn, teeth 36 of body 2 prevent the return of tail 33, and teeth 37 of the pusher can disengage from notches 34 of the tail to allow the pusher to return rearward.

The operation of the instrument, from the configuration in FIG. 1, is the following. With the instrument first detached from the support on which it will eventually be attached by a clip 40 incorporated into pusher 22, the volume of the liquid dose to be injected is adjusted. By rotating the pusher, effected by a circumferential movement of pointer 25, the latter is brought opposite the chosen volume, indicated by a marking 26 on body 2. Simultaneously, pin 27 moves, entering then bypassing the various slots 14 to 21 until it penetrates the slot corresponding to the volume chosen by the user. By pulling on pusher 22, the user loads the instrument until pin 27 abuts the top end of the slot 14–21 in which it is located. When this extraction takes place, teeth 37 of the pusher slide along rack 33.

The user then removes cap 13, and perforates stopper 9 with a needle 10, unless this has already been done, before making the injection. Pressure on pusher 22 results in displacement in reference direction 8 of this pusher, of tail 33, and of plunger 7, which drives liquid 6 contained in reservoir 5. This movement is not disturbed by teeth 36 of the body which allow the notches of the tail to pass because of the respective inclinations of teeth 37 and notches 34.

Figure 5:
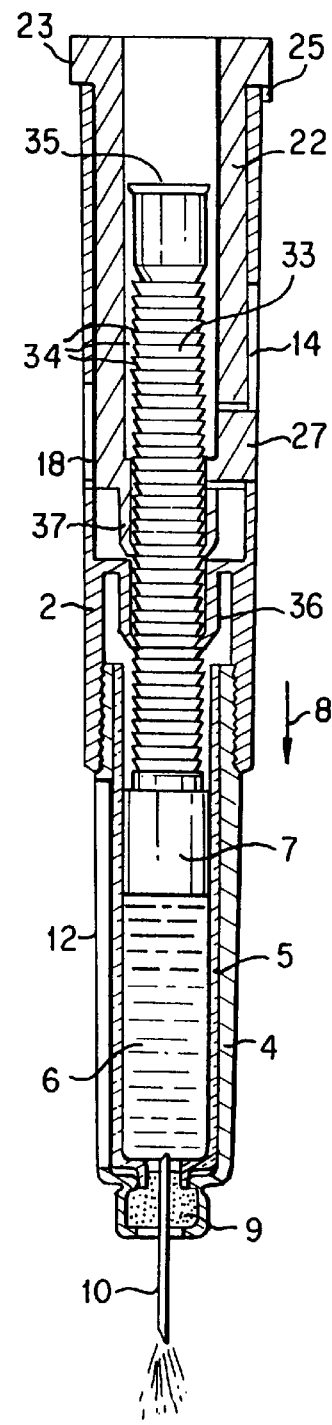

Loading of the instrument is shown in FIG. 4, while the end of injection corresponds to the position of FIG. 5. At the end of injection, collar 23 of pusher abuts the upper edge of body 2. Once the injection is complete, cap 13 is replaced on the front end of the instrument.

Figure 6:
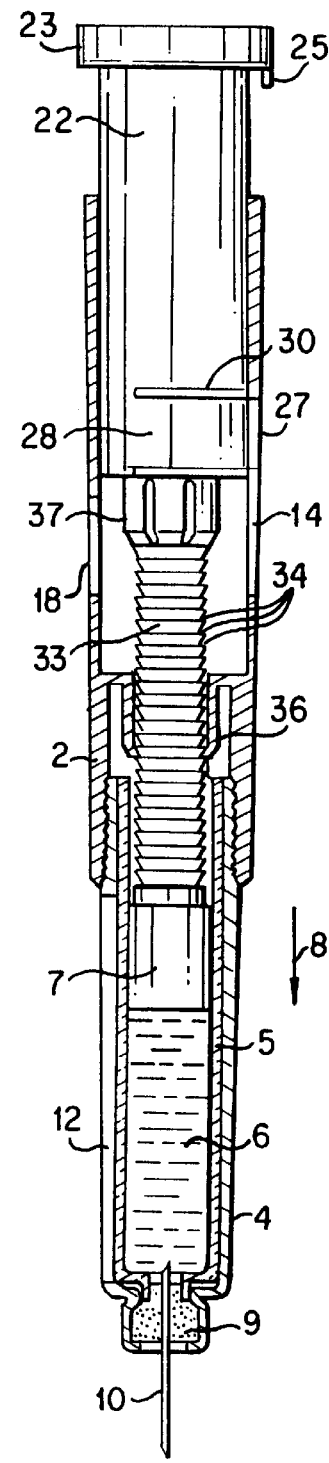
FIG. 6 is a lengthwise view of the instrument, with the exception of the pusher which is seen in a side view.

FIG. 6 shows the instrument with the tail 33 in the same position as in FIG. 5, and with the pusher 22 being viewed from the outside and having been extended upward to the same position as in FIG. 4.

It should be noted that collar 35 of tail 33 of the instrument makes it impossible to reload the instrument properly when the volume of liquid contained in reservoir 5 is less than the volume of the dose to be injected. Moreover, once the reservoir has been removed, this collar prevents tail 33 from being released to move forward with a view to reuse of the instrument.

It emerges from the foregoing that the instrument according to the invention is simple in design since it has three parts made of synthetic material, namely a body, a pusher, and a tail, which carry out the functions of dose adjustment, visualization of operations, and prevention of return when these three parts move relative to each other. They are simple parts assembled merely by fitting together, whose utilization is simple and quite safe, even in an emergency or when used by a physically limited person.

I claim:

1. A metering instrument, comprising:
a body;
a liquid reservoir connected to said body;
a plunger displaceable in said reservoir along a reference direction;
a perforable stopper closing off an other end of the reservoir through which a dose of the liquid passes;
a pusher movable translationally inside the body;
a tail mounted inside the pusher, said tail having a rack and being movable translationally with the pusher, wherein the tail and pusher are engaged such that when the pusher moves translationally with respect to the tail, the pusher does not rotate substantially with respect to the tail;

a first ratchet device disposed on the body, said first ratchet device being in engagement with the rack, wherein the engagement between the body and the rack prevents the tail from moving in a direction opposite the reference direction; and a second ratchet device disposed on the pusher, said second ratchet device being in engagement with said rack, wherein the body includes a plurality of axial slots of different lengths, said pusher having a pin in selective engagement with at least one of said slots in the body.

2. A metering instrument according to claim 1, wherein said rack includes a plurality of notches, and the length of each axial slot permits said pin to travel through a length equal to a whole number multiplied by the length of one of said notches.

3. A metering instrument according to claim 1, wherein said pusher is mounted for rotational movement in said body, and the pin projects from an outer surface of the pusher and is designed to retract radially when said pusher is rotated inside the body is introduced inside body.

4. A metering instrument according to claim 3, wherein the pin comprises a tongue and an axial rib that projects outward from a free end of the tongue, said tongue being delimited in the wall of the pusher by an axial slot and two circumferential slots in the wall extending over part of the periphery of the pusher.

5. A metering instrument according to claim 4, wherein said rib has first and second edges, said first edge being located downstream of said second edge with respect to said reference direction, said first edge being rounded, and said second edge being straight and perpendicular to an axis of the pusher.

6. A metering instrument according to claim 3, wherein said pin is designed to retract when said pusher is inserted in the reference direction into said body.

7. A metering instrument according to claim 1, wherein said pusher includes an end projecting outside of said body.

8. A metering instrument according to claim 7, wherein the end of the pusher projecting outside the body is activatable by a user and is equipped with a collar designed to abut an edge of the body at the end of the travel of said pusher.

9. A metering instrument according to claim 8, wherein the plurality of axial slots provided in said body have first ends located in a plane perpendicular to the axis of the body, the distance between said plane and the collar abutting edge of the body being greater than the distance between a first edge of said pin and said collar.

10. A metering instrument according to claim 8, wherein the collar is equipped with a pointer aligned with the pin, said pointer being designed, at the end of the travel of the pusher, to cover the outer wall of the body opposite a marking of the body.

11. A metering instrument according to claim 1, wherein said body is tubular.

12. A metering instrument according to claim 1, wherein the liquid reservoir comprises a tubular wall having an open end, and the plunger forms a seal to close said open end of said tubular wall.

13. A metering instrument according to claim 1, wherein said reservoir includes an open end through which a dose of liquid is ejected, said metering instrument further comprising a perforable stopper closing said open end of said liquid reservoir.

14. A metering instrument according to claim 1, wherein the pusher is tubular and is mounted coaxially with said body.

15. A metering instrument according to claim 1, wherein said rack comprises a plurality of successive annular notches.

16. A metering instrument according to claim 15, wherein said plurality of annular notches are arranged over a length at least equal to the plunger travel necessary for emptying the reservoir.

17. A metering instrument according to claim 15, wherein each notch has a generally frustroconical shape having a small section, wherein the small section points toward an end of said tail abutting said plunger.

18. A metering instrument according to claim 17, wherein the first and second ratchet devices are formed by two series of teeth molded onto the body and the pusher respectively, each tooth being oriented radially inward and inclined in the direction of the reservoir, the ends of the teeth in a series being disposed in a plane perpendicular to the axis of one of the body and the pusher, and each tooth being designed to penetrate between two successive notches of the rack.

19. A metering instrument according to claim 1, wherein said plurality of axial slots are disposed about the periphery of the body.

20. A metering instrument according to claim 1, wherein each length of said axial slots corresponds to the length of permitted translational movement of the pusher.

21. A metering instrument according to claim 1, wherein one end of said tail abuts the plunger.

22. A metering instrument according to claim 21, wherein an end of said tail opposite the end abutting said plunger is equipped with a collar having an outside diameter that is less than the inside diameter of the pusher, said collar being sized so as to prevent said tail from passing completely through said second ratchet device.

* * * * *